(12) United States Patent
Matsuo et al.

(10) Patent No.: US 10,206,439 B2
(45) Date of Patent: Feb. 19, 2019

(54) ELBOW JOINT SUPPORTER

(75) Inventors: Kazuhiko Matsuo, Tokyo (JP);
Hidefumi Koga, Gose (JP)

(73) Assignee: KOWA COMPANY, LTD., Nagoya-Shi (JP)

( * ) Notice: Subject to any disclaimer, the term of this patent is extended or adjusted under 35 U.S.C. 154(b) by 7 days.

(21) Appl. No.: 13/522,670

(22) PCT Filed: Jan. 24, 2011

(86) PCT No.: PCT/JP2011/051221
§ 371 (c)(1),
(2), (4) Date: Jul. 17, 2012

(87) PCT Pub. No.: WO2011/090195
PCT Pub. Date: Jul. 28, 2011

(65) Prior Publication Data
US 2012/0289875 A1    Nov. 15, 2012

(30) Foreign Application Priority Data

Jan. 22, 2010 (JP) .................................. 2010-012513

(51) Int. Cl.
*A41D 13/08* (2006.01)
*A61F 5/01* (2006.01)
(Continued)

(52) U.S. Cl.
CPC ............ *A41D 13/08* (2013.01); *A61F 5/0118* (2013.01); *A61F 13/101* (2013.01); *A63B 71/12* (2013.01); *A63B 2071/125* (2013.01)

(58) Field of Classification Search
USPC .............................. 602/60–63; 2/16; 128/881
See application file for complete search history.

(56) References Cited

U.S. PATENT DOCUMENTS 3,000,318 A * 9/1961 Zieman .............. F02M 41/1411
  417/206
3,000,378 A * 9/1961 Zieman ................... A61F 13/10
  2/16
(Continued)

FOREIGN PATENT DOCUMENTS

CN        1102317 A      5/1995
CN        2855127 Y      1/2007
(Continued)

OTHER PUBLICATIONS

Rehfeldt, Janet; "Machine Knit Tips and Techniques! Plating Tips"; Feb 1, 2001.*
(Continued)

*Primary Examiner* — Ophelia A Hawthorne
*Assistant Examiner* — Caitlin Carreiro
(74) *Attorney, Agent, or Firm* — Duquette Law Group, LLC

(57) ABSTRACT

An elbow joint supporter includes a first anchor section formed by wrapping one end of a tubular knitted fabric around the wearer's upper arm, a second anchor section formed by wrapping the other end of the fabric around the wearer's forearm, and a substantially X-shaped knitted supporting section intersecting at the wearer's cubital fossa. Two ends of the X-shaped knitted fabric are joined to the first anchor section and the other two ends of the X-shaped knitted fabric are joined to the second anchor section so as to support the wearer's elbow joint. In the circumferential direction of the fabric, the stretch resistances of the first anchor part and the second anchor part are larger than that of a base fabric section. In the length direction of the fabric, the stretch resistance of the supporting section is larger than that of the base fabric section.

16 Claims, 9 Drawing Sheets

(51) Int. Cl.
*A61F 13/10* (2006.01)
*A63B 71/12* (2006.01)

(56) References Cited

U.S. PATENT DOCUMENTS

| | | | |
|---|---|---|---|
| 3,084,685 A | | 4/1963 | Lewis |
| 3,934,583 A | * | 1/1976 | Hollingshead ........ A61F 5/0585 602/62 |
| 4,315,504 A | * | 2/1982 | Drennan et al. ............. 128/892 |
| 4,492,227 A | | 1/1985 | Senn et al. |
| 7,434,423 B1 | * | 10/2008 | Reid, Jr. ................. A61F 13/08 66/178 A |

FOREIGN PATENT DOCUMENTS

| | | | |
|---|---|---|---|
| CN | 2865338 Y | | 2/2007 |
| GB | 2 241 647 | | 9/1991 |
| JP | 2001037803 A | | 2/2001 |
| JP | 2002266125 A | * | 9/2002 |
| JP | 2003286606 A | | 10/2003 |
| JP | 2007054126 A | * | 3/2007 |
| JP | 2010-100981 | | 5/2010 |
| JP | 2010131066 A | | 6/2010 |
| TW | 200836651 A | | 9/2008 |
| TW | I339226 B | | 3/2011 |

OTHER PUBLICATIONS

Gifford, Shannon; "Mesh Knits and Power Mesh"; Oct. 28, 2007.*
Machine Translation of JP2007054126; accessed from www.jpo.go.jp.*
"JP2002-266125_mchtranslation.PDF"; English machine translation of JP2002-266125.*
Rehfeldt reference.*
Gifford reference.*
Machine translation of JP2007054126.*
Machine translation of JP2002266125.*
Translation of JP 2007054126 A.*
Translation of JP 2002266125 A.*
Rehfeldt ("Machine Knit Tips and Techniques! Plating Tips").*
Gifford ("Mesh Knits and Power Mesh").*
English translation of JP 2007054126 A.*
English translation of JP 2002266125 A.*
International Search Report of International Application No. PCT/JP2011/051221 dated Mar. 22, 2011.
The Japanese Association of Rehabilitation Medicine, "Method of Measuring and Indicating Range of Joint Motion", vol. 32, No. 4, 1995, pp. 207-217 (English explanation of description of elbow movement range on p. 210 and description of knee movement range on p. 213).
European Search Report of European Application No. EP 11734801.1, dated Dec. 12, 2013.

* cited by examiner

Fig. 1a
Fig. 1c
Fig. 1b
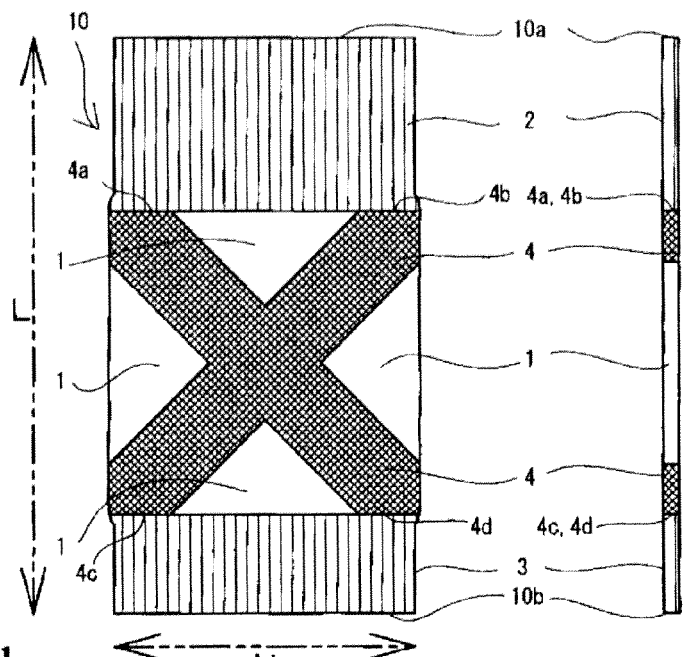
Fig. 1d
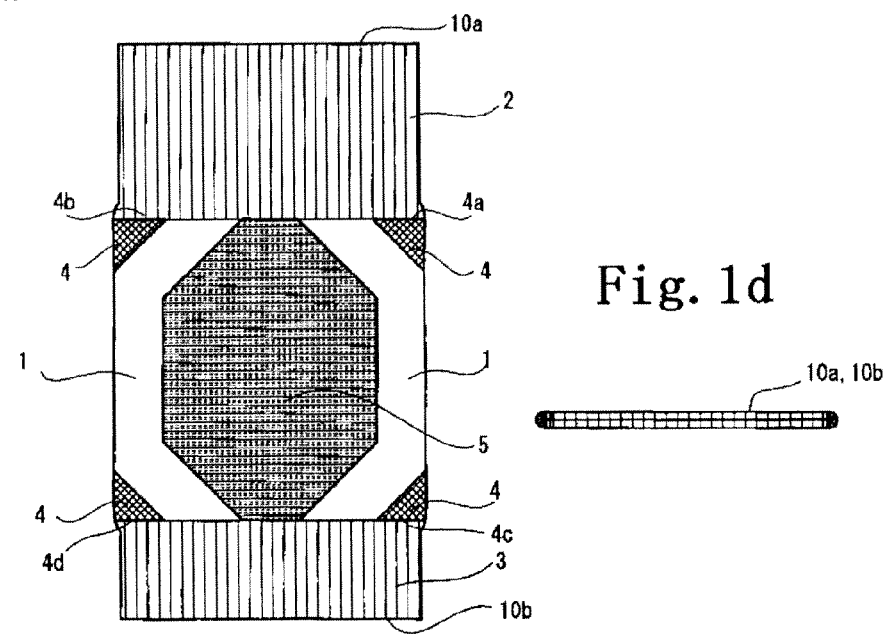

Fig. 8a
Fig. 8c
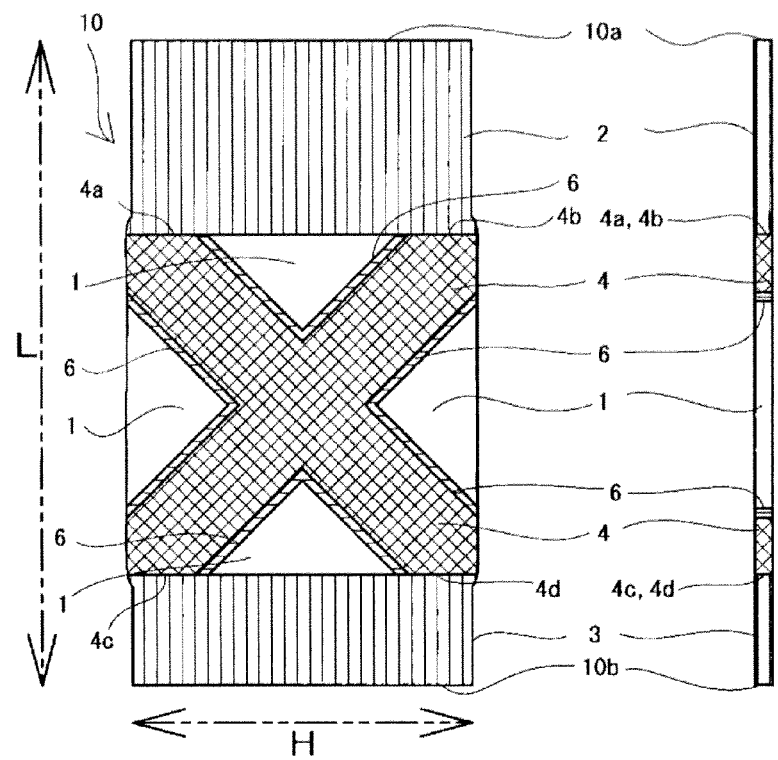
Fig. 8b
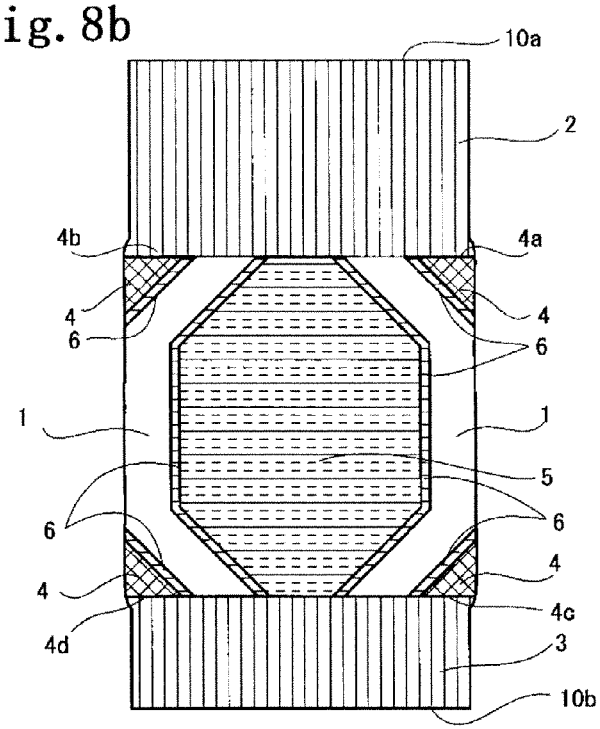
Fig. 8d
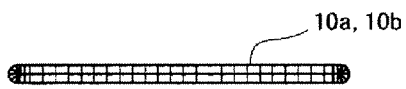

Fig. 9a
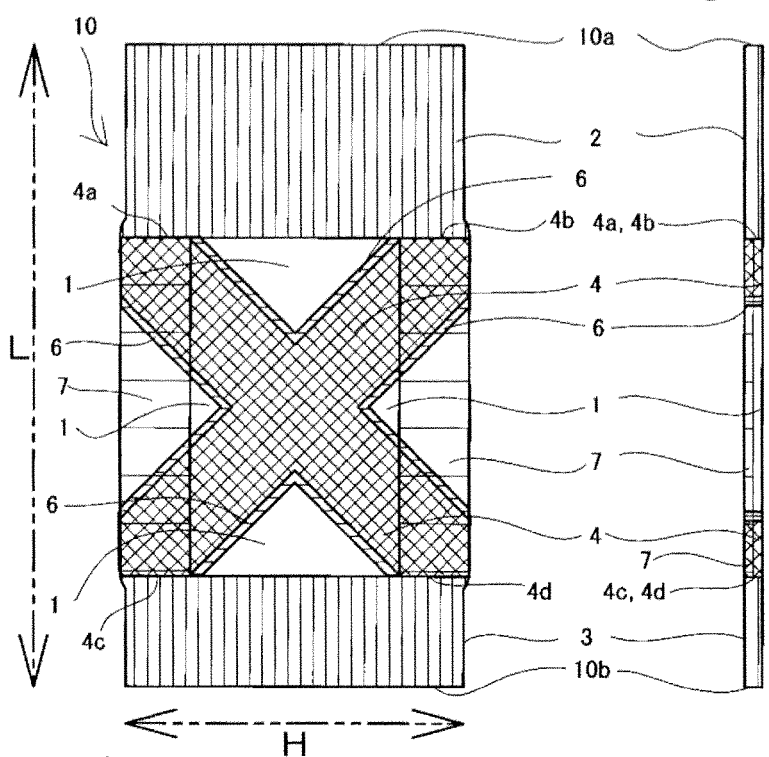
Fig. 9c
Fig. 9b
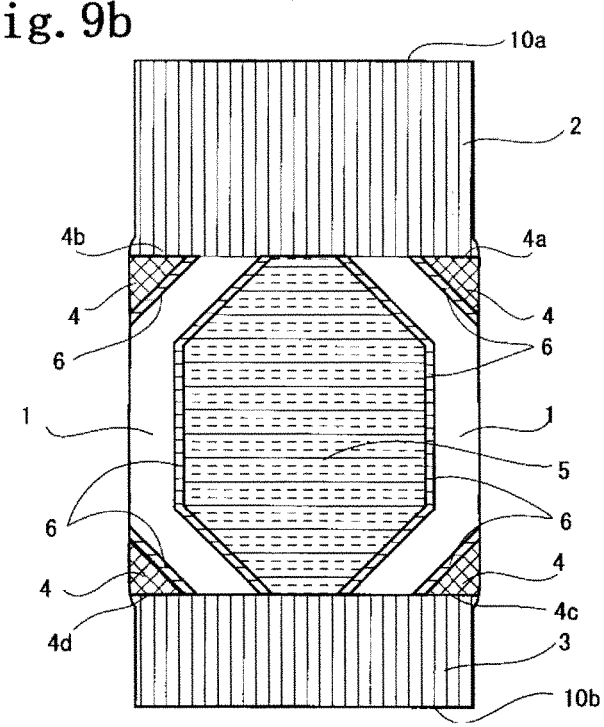
Fig. 9d

ELBOW JOINT SUPPORTER

TECHNICAL FIELD

The present invention relates to an elbow joint supporter which can support a wearer's daily motion, and particularly, to an elbow joint supporter having a taping function of improving the stability of the elbow joint, thereby reducing a strain on the elbow joint and also reducing a load on the biceps brachii tendon.

BACKGROUND ART

If the motion of fully extending the elbow joint is repeated in a sports motion or the like, a pain occurs in the vicinity of the olecranon. Inflammation of the joint capsule is often regarded as a factor of the pain, and in severe cases, the formation of an osteophyte or a bone fracture occurs. Further, a main motion muscle to bend the elbow joint is the biceps brachii muscle. In the biceps brachii muscle, if a flexion motion of the elbow joint due to load transportation or the like is repeatedly performed, inflammation occurs in the biceps brachii tendon extending in front of the shoulder joint, thereby causing a pain. In particular, a load in an extension direction of the elbow joint (the eccentric contraction of the biceps brachii tendon) becomes an overload.

Regarding this, a supporter for an elbow in the related art includes a tubular supporter main body which covers at least the upper and lower sides of the elbow joint of the arm of a wearer, first and second expansion and contraction inhibition sections each provided over an approximately half circumference at a periphery of one end of the supporter main body, and third and fourth expansion and contraction inhibition sections each provided over an approximately half circumference at the peripheral surface of the other end, wherein the first and second expansion and contraction inhibition sections and the third and fourth expansion and contraction inhibition sections are respectively disposed at about 90° torsional positions such that the first expansion and contraction inhibition section presses the biceps brachii muscle, the second expansion and contraction inhibition section presses the triceps brachii muscle, the third expansion and contraction inhibition section presses the brachioradial muscle, the extensor carpi radialis longus muscle, the extensor carpi radialis brevis muscle, and the extensor carpi ulnaris muscle, and the fourth expansion and contraction inhibition section presses the flexor carpi radialis muscle and the extensor carpi ulnaris muscle (refer to PTL 1, for example).

CITATION LIST

Patent Literature

[PTL 1] JP-A-2003-286606

SUMMARY OF INVENTION

Technical Problem

The supporter for an elbow in the related art is a supporter activating the muscles of the arm or the wrist of a wearer and the expansion and contraction inhibition section extends in the circumferential direction of the arm of the wearer to press the muscles. However, an expansion and contraction inhibition section does not extend in the length direction of the arm of the wearer. For this reason, the supporter for an elbow in the related art is not for controlling the full extension of the elbow joint (limiting a range of motion) and cannot reduce a strain on the elbow joint, so that there is a problem in that it is not possible to prevent inflammation of the biceps brachii tendon.

In particular, in the supporter for an elbow in the related art, since the first to fourth expansion and contraction inhibition sections are constituted by resin or rubber, there is a problem in that after the tubular main body is constituted, a process of printing resin or rubber on the expansion and contraction inhibition sections needed, so that a manufacturing process is complicated.

The present invention has been made to solve the problems as described above and has an object to provide an elbow joint supporter which improves the stability of the elbow joint, thereby being able to reduce a strain on the elbow joint and also reduce a load on the biceps brachii tendon.

Solution to Problem

An elbow joint supporter according to the invention includes: a first anchor section which is knitted to go around one end of a tubular knitted fabric and makes the tubular knitted fabric be tightened on the brachium of a wearer; a second anchor section which is knitted to go around the other end of the tubular knitted fabric and makes the tubular knitted fabric be tightened on the forearm of the wearer; and a supporting section which is knitted in an approximate X-shape that crosses at the cubital fossa of the wearer, and supports the elbow joint of the wearer by connecting two end portions in the approximately X-shaped knitted fabric to the first anchor section and connecting the other two end portions in the approximately X-shaped knitted fabric to the second anchor section, wherein the stretch resistances of the first anchor section and the second anchor section in a circumferential direction of the tubular knitted fabric are larger than the stretch resistance of a base fabric section in the circumferential direction of the tubular knitted fabric, and the stretch resistance of the supporting section in a length direction of the tubular knitted fabric is larger than the stretch resistance of the base fabric section in the length direction of the tubular knitted fabric.

Advantageous Effects of Invention

In the elbow joint supporter according to the invention, by controlling the full extension of the elbow joint, it is possible to reduce a load on the olecranon (the rear of the elbow joint) and also protect the biceps brachii tendon and reduce a pain.

BRIEF DESCRIPTION OF DRAWINGS

FIG. 1(a) is a front view showing the schematic configuration of an elbow joint supporter related to the first embodiment, FIG. 1(b) is a back view of the elbow joint supporter shown in FIG. 1(a), FIG. 1(c) is a left side view and right side view of the elbow joint supporter shown in FIG. 1(a), and FIG. 1(d) is a plan view and bottom view of the elbow supporter shown in FIG. 1(a).

FIG. 8(a) is a front view showing the schematic configuration of another elbow joint supporter related to the first embodiment, FIG. 8(b) is a back view of the elbow joint supporter shown in FIG. 8(a), FIG. 8(c) is a left side view and right side view of the elbow joint supporter shown in FIG. 8(a), and FIG. 8(d) is a plan view and bottom view of the elbow supporter shown in FIG. 8(a).

FIG. 9(a) is a front view showing the schematic configuration of an elbow joint supporter related to the second embodiment, FIG. 9(b) is a back view of the elbow joint supporter shown in FIG. 9(a), FIG. 9(c) is a left side view and right side view of the elbow joint supporter shown in FIG. 9(a), and FIG. 9(d) is a plan view and bottom view of the elbow supporter shown in FIG. 9(a).

DESCRIPTION OF EMBODIMENTS (First Embodiment of the Invention)

Figure 2A:
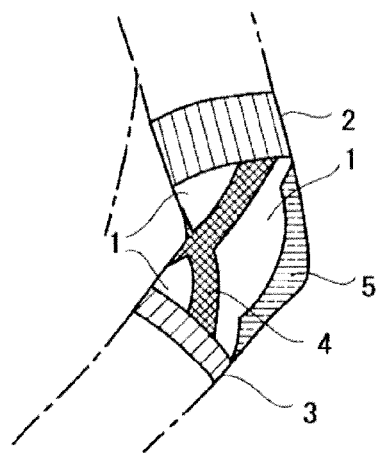
FIG. 2(a) is a perspective view showing a wearing state of the elbow joint supporter shown in FIG. 1.
Figure 2B:
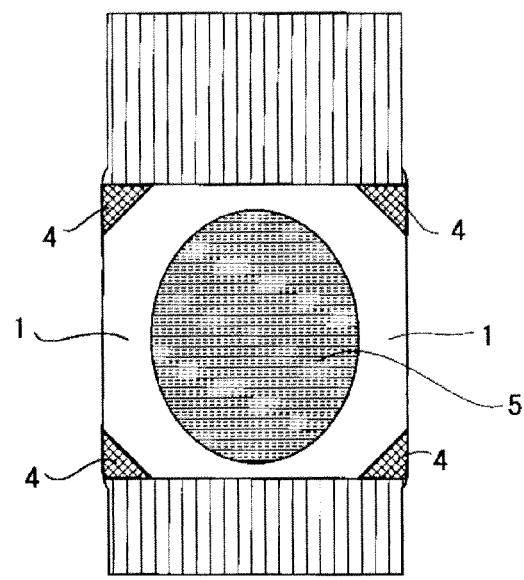
FIG. 2(b) is a back view showing another schematic configuration of the elbow joint supporter shown in FIG. 1(a)
Figure 2C:
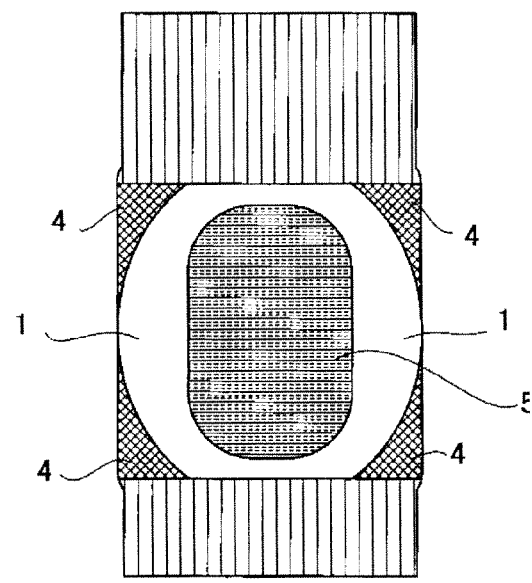
FIG. 2(c) is a back view showing still another schematic configuration of the elbow joint supporter shown in FIG. 1(a).

In FIG. 1, 2, or 8, an elbow joint supporter 10 is made of a tubular knitted fabric which is knitted in circular knitting by a hosiery knitting machine (for example, a type of knitting machine (the number of needles: 256) manufactured by Lonati Co.), and is a supporter which comes into close contact with the body surface of a wearer, thereby assisting the elbow joint of the wearer.

The elbow joint supporter 10 has a desired functionality such as a taping function by performing different knitting with respect to a base fabric section 1 that is a knitted fabric which is knitted in a plain stitch, a rib stitch, a tuck stitch, a float stitch, a pile stitch, or the like by using an upper thread, an under thread, and a rubber thread as knitting yarn. In addition, the base fabric section 1 related to this embodiment is a knitted fabric which is knitted in a tuck stitch (hereinafter referred to as a tuck stitch knitted fabric).

In addition, the tuck stitch knitted fabric is a knitted fabric in which a certain loop is not made temporarily when knitting the fabric and loops are made together when knitting the next course. In addition, in this embodiment, in consideration of a balance with density, the number of times to tuck is set to be twice. However, the number of times is not limited thereto.

Further, the elbow joint supporter 10 has a first anchor section 2 which is knitted to go around one end (an upper end 10a) of the tubular knitted fabric and makes the elbow joint supporter 10 be tightened on the brachium of a wearer, and a second anchor section 3 which is knitted to go around the other end (a lower end 10b) of the tubular knitted fabric and makes the elbow joint supporter 10 be tightened on the forearm of the wearer.

The first anchor section 2 and the second anchor section 3 are knitted such that the stretch resistances thereof in a circumferential direction H of the elbow joint supporter 10 (the tubular knitted fabric) are larger than the stretch resistance of the base fabric section 1 in the circumferential direction H of the elbow joint supporter 10. That is, when tension in a case where certain elongation has been imparted from a state where elongation is not imparted to a material is set to be F, the tension of the base fabric section 1 in the circumferential direction H of the elbow joint supporter is set to be $F_{H1}$, the tension of the first anchor section 2 in the circumferential direction H of the elbow joint supporter 10 is set to be $F_{H2}$, and the tension of the second anchor section 3 in the circumferential direction H of the elbow joint supporter 10 is set to be $F_{H3}$, the first anchor section 2 and the second anchor section 3 have such a magnitude relation of $F_{H2} \approx F_{H3} > F_{H1}$ that they have strong tightening forces in the circumferential direction H of the elbow joint supporter 10, compared to the base fabric section 1.

Specifically, by making each of the first anchor section 2 and the second anchor section 3 be a knitted fabric knitted in a moss stitch (hereinafter referred to as a moss stitch knitted fabric), it is possible to make the stretch resistance thereof in the circumferential direction H of the elbow joint supporter 10 large with respect to the base fabric section 1 that is the tuck stitch knitted fabric.

In addition, the moss stitch knitted fabric is a knitted fabric in which a plain stitch and a tuck (a structure in which no loop protrudes over a certain course and plural loops protrude over the subsequent course) appear alternately or for every few courses in the course direction and the wale direction. For this reason, in each of the first anchor section 2 and the second anchor section 3, the plain stitch and the tuck are used in combination, whereby it is possible to make protuberances or openwork stitches on the surface of a knitted fabric and a mesh pattern such as a moss appear.

In this manner, the first anchor section 2 is knitted to surround the brachium of a wearer, and the stretch resistance of the first anchor section 2 in the circumferential direction H of the elbow joint supporter 10 is larger than the stretch resistance of the base fabric section 1 in the circumferential direction H of the elbow joint supporter 10, whereby it is possible to fix the elbow joint supporter 10 to the brachium of a wearer and suppress slipping-off of the upper end 10a of the elbow joint supporter 10 at the time of the flexion of the elbow joint. Further, the first anchor section 2 is connected to a supporting section 4 (described later), thereby also functioning as an anchor of the supporting section 4.

Further, the second anchor section 3 is knitted to surround the forearm of a wearer, and the stretch resistance of the second anchor section 3 in the circumferential direction H of the elbow joint supporter 10 is larger than the stretch resistance of the base fabric section 1 in the circumferential direction H of the elbow joint supporter 10, whereby it is possible to fix the elbow joint supporter 10 to the forearm of a wearer and suppress slipping-off of the lower end 10b of the elbow joint supporter 10 at the time of the flexion of the elbow joint. Further, the second anchor section 3 is connected to the supporting section 4 (described later), thereby also functioning as an anchor of the supporting section 4.

In addition, if the tightening forces on the brachium and the forearm of a wearer by the first anchor section 2 and the second anchor section 3 are too strong, constriction of blood flow in the brachium and the forearm occurs, thereby causing a feeling of discomfort to the wearer. In particular, the feeling of discomfort is marked in the brachium, compared to the forearm.

For this reason, in the elbow joint supporter 10 related to this embodiment, the feeling of discomfort which is imparted to a wearer is alleviated by widening the area of the first anchor section 2 which comes into contact with the body surface of the wearer, with respect to the second anchor section 3, thereby dispersing pressure which is applied to the body surface by the first anchor section 2, and also adjusting density in a portion of the first anchor section 2 (for example, to make a tightening force thereof be reduced by about 10% with respect to the second anchor section 3). That is, it is preferable that the elbow joint supporter 10 related to this embodiment have a magnitude relation of $F_{H3} > F_{H2} > F_{H1}$ so as to have a moderate tightening force in the circumferential direction H of the elbow joint supporter 10.

The supporting section 4 is knitted in an approximate X-shape which crosses at the cubital fossa of a wearer, and supports the elbow joint of the wearer by connecting two end portions 4a and 4b in an approximately X-shaped knitted fabric to the first anchor section 2 and connecting the other two end portions 4c and 4d in the approximately X-shaped knitted fabric to the second anchor section 3. That is, the supporting section 4 is locked at the first anchor section 2 on the brachium side of a wearer and locked at the second anchor section 3 on the forearm side of the wearer.

Further, it is preferable that the supporting section 4 be formed such that the stretch resistance in the length direction of the supporting section 4 becomes large compared to the stretch resistance in the width direction of the supporting section 4. However, it is difficult to knit a knitted fabric with a difference in the stretch resistance imparted thereto, by circular knitting. Therefore, in this embodiment, the supporting section 4 is formed in which the stretch resistance thereof in a length direction L of the elbow joint supporter 10 is large compared to the stretch resistance thereof in the circumferential direction H of the elbow joint supporter 10 so as to approximate to a knitted fabric with a difference in the stretch resistance imparted thereto.

Further, the supporting section 4 is knitted such that the stretch resistance thereof in the length direction L of the elbow joint supporter 10 is larger than the stretch resistance of the base fabric section 1 in the length direction L of the elbow joint supporter 10. That is, when the tension of the base fabric section 1 in the length direction L of the elbow joint supporter 10 is set to be $F_{L1}$ and the tension of the supporting section 4 in the length direction L of the elbow joint supporter 10 is set to be $F_{L4}$, the supporting section 4 has such a magnitude relation of $F_{L4} > F_{L1}$ that it has a strong tightening force in the length direction L of the elbow joint supporter 10, compared to the base fabric section 1.

Specifically, by making the supporting section 4 be a knitted fabric in which a tuck stitch and a plating stitch are used in combination (hereinafter referred to as a tuck stitch-plating stitch knitted fabric), it is possible to make the stretch resistance thereof in the length direction L of the elbow joint supporter 10 large with respect to the base fabric section 1 that is the tuck stitch knitted fabric.

In addition, in the tuck stitch-plating stitch knitted fabric, expansion and contraction of the supporting section 4 in the length direction L of the elbow joint supporter 10 is moderately suppressed by additionally feeding another knitting yarn (for example, woolly nylon yarn) in addition to ground knitting yarn of the tuck stitch, and another knitting yarn is cut at the boundary between the supporting section 4 and the base fabric section 1 (a cut boss).

In this manner, the supporting section 4 is knitted in an approximate X-shape which crosses at the cubital fossa of a wearer, and the stretch resistance thereof in the length direction L of the elbow joint supporter 10 is larger than the stretch resistance of the base fabric section 1 in the length direction L of the elbow joint supporter 10, whereby it is possible to grip the elbow joint like grabbing the cubital fossa of a wearer, thereby limiting the rotation of the elbow joint and securing the stability of the elbow joint, and it is also possible to prevent damage to the ligament which is located at the elbow joint due to over-rotation of the elbow joint. Since in particular, in the cubital fossa of a wearer, a range of joint motion of flexion and extension of the elbow joint with respect to the entire elbow is the widest, if the area of the supporting section 4 in the cubital fossa is too wide, a state is created where the supporting section 4 with large stretch resistance becomes a large mass and is superimposed on a section of the cubital fossa of the wearer. For this reason, in this embodiment, by making the area of the supporting section 4 in the cubital fossa as small as possible by forming the supporting section 4 into an approximate X-shape which crosses at the cubital fossa of a wearer, it becomes possible to make a mass by the supporting section 4 with large stretch resistance superimposed on a section of the cubital fossa of the wearer as small as possible, so that it is possible to enhance a fitting feeling of the elbow joint supporter 10.

Further, special function knitting (the tuck stitch-plating stitch knitted fabric) in the supporting section 4 is connected to the moss stitch knitted fabrics in the first anchor section 2 and the second anchor section 3 and prevents a position shift of the supporting section 4 with respect to the cubital fossa of a wearer, so that it is possible to fix the supporting section 4 to an appropriate position.

An olecranon contact section 5 is a section which is knitted on the rear face side of the elbow joint supporter 10 and comes into contact with the olecranon of a wearer, and in this embodiment, the olecranon contact section 5 is an approximately octagon-shaped knitted fabric.

The olecranon contact section 5 is knitted such that the stretch resistance thereof in the length direction L of the elbow joint supporter 10 is smaller than the stretch resistance of the base fabric section 1 in the length direction L of the elbow joint supporter 10. That is, when the tension of the olecranon contact section 5 in the length direction L of the elbow joint supporter 10 is set to be $F_{L5}$, the olecranon contact section 5 has such a magnitude relation of $F_{L1} > F_{L5}$ that it has a weak tightening force in the length direction L of the elbow joint supporter 10, compared to the base fabric section 1.

Specifically, by making the olecranon contact section 5 be a knitted fabric knitted in a mesh stitch that is a knitting structure having good air permeability (hereinafter referred to as a mesh stitch knitted fabric), it is possible to make the stretch resistance thereof in the length direction L of the elbow joint supporter 10 small with respect to the base fabric section 1 that is the tuck stitch knitted fabric.

In addition, the mesh stitch knitted fabric is a knitted fabric in which a certain loop is not made temporarily when knitting the fabric and loops are made together when knitting the next course and which stretches well with knitting in the form of a mesh.

In this manner, the olecranon contact section 5 is a section which comes into contact with the olecranon of a wearer, and the stretch resistance thereof in the length direction L of the elbow joint supporter 10 is smaller than the stretch resistance of the base fabric section 1 in the length direction L of the elbow joint supporter 10, whereby forces associated with expansion and contraction of the skin of a wearer in the bending and stretching motion or the rotation motion of the elbow joint can be absorbed by a high stretch function. In particular, the olecranon contact section 5 can grip the kneecap of a wearer at the time of the flexion of the elbow joint due to the mesh stitch knitted fabric having high stretch properties, and prevents a position shift in any direction of the elbow joint supporter 10, so that it is possible to improve the operation and effects by the supporting section 4 described above, as an anchor function of the supporting section 4.

In particular, the olecranon contact section 5 may also be a knitted fabric in which a mesh stitch knitted fabric (a plain stitch knitted fabric composed of an under thread and a rubber thread without feeding an upper thread) and a plain stitch knitted fabric (a plain stitch knitted fabric composed of an upper thread, an under thread, and a rubber thread), which extend in the circumferential direction H of the elbow joint supporter 10, are alternately arranged in parallel (hereinafter referred to as a bellows knitted fabric).

In this case, in the bellows knitted fabric, since the surface of the elbow joint supporter 10 is nearly flat, but the thickness of the mesh stitch knitted fabric is thin with respect to the plain stitch knitted fabric, the part of the mesh stitch knitted fabric becomes a concave portion, so that a concavity and a convexity are created on the rear surface of the elbow joint supporter 10. For this reason, the olecranon contact section 5 becomes a knitted fabric having high stretch properties, because frictional resistance between the olecranon of a wearer and the olecranon contact section 5 is small due to a narrow contact area with the body surface of the wearer and frictional resistance between adjacent threads is also small due to the large loop of the mesh stitch knitted fabric.

In addition, with respect to the shape of the olecranon contact section 5 related to this embodiment, it is possible to adopt a knitted fabric having an approximate octagon shape (refer to FIG. 1(*b*)), a circular or ellipse shape (refer to FIG. 2(*b*)), or an oval shape (refer to FIG. 2(*c*)) to fit the shape of the olecranon of a wearer. In particular, the knitted fabric of a circular shape, an ellipse shape, or an oval shape improves a grip performance on the olecranon of a wearer, thereby preventing a position shift in any direction of the elbow joint supporter 10, so that it is possible to maintain the reliable mounting state of the elbow joint supporter 10.

In addition, in the elbow joint supporter 10 related to this embodiment, due to the knitted fabric of each site described above, the stretch resistance of the base fabric section 1 in the length direction L of the elbow joint supporter 10 is larger than the stretch resistance of the second anchor section 3 in the length direction L of the elbow joint supporter 10. Further, the stretch resistance of the second anchor section 3 in the length direction L of the elbow joint supporter 10 is larger than the stretch resistance of the first anchor section 2 in the length direction L of the elbow joint supporter 10. Further, the stretch resistance of the first anchor section 2 in the length direction L of the elbow joint supporter 10 is larger than the stretch resistance of the olecranon contact section 5 in the length direction L of the elbow joint supporter 10.

Therefore, the elbow joint supporter 10 related to this embodiment satisfies a magnitude relation shown by the following expression (1) in the tension F in the length direction L of the elbow joint supporter 10. However, in the following expression (1), $F_{L2}$ is the tension of the first anchor section 2 in the length direction L of the elbow joint supporter 10, and $F_{L3}$ is the tension of the second anchor section 3 in the length direction L of the elbow joint supporter 10.

[Expression 1]

$$F_{L4} > F_{L1} > F_{L3} > F_{L2} > F_{L5} \qquad (1)$$

In particular, the tensions $F_{L1}$ and $F_{L4}$ in the length direction L of the elbow joint supporter 10 of the base fabric section 1 and the supporting section 4 which occupy the entire area on the front face side of the elbow joint supporter 10 excluding the first anchor section 2 and the second anchor section 3 are larger than the tension $F_{L5}$ in the length direction L of the elbow joint supporter 10 of the olecranon contact section 5 which occupies almost the entire area on the rear face side of the elbow joint supporter 10, whereby the elbow joint supporter 10 has the following operation and effects.

The base fabric section 1 and the supporting section 4 which are on the front face side of the elbow joint supporter 10 suppress the extension in the length direction L of the elbow joint supporter 10 and perform a limitation such that the extended position of the elbow joint does not exceed 180 degrees (hyperextension does not occur), by a difference contraction between the sections and the olecranon contact section 5 that is a high stretchable mesh stitch knitted fabric, so that it is possible to limit the extension of the ligament which is located at the elbow joint.

That is, the elbow joint supporter 10 prevents damage to the ligament by an excessive extension of the ligament which is located at the elbow joint, and also protects the biceps brachii muscle that controls the extension of the elbow joint, so that it is possible to reduce a pain due to bicipital tendinitis. In particular, the base fabric section 1 and the supporting section 4 which are on the front face side of the elbow joint supporter 10 can act like a splint which supports the elbow joint from the front face side, thereby suppressing the shake of the bending and stretching motion of the elbow joint.

Further, in a case where the elbow joint supporter 10 is not worn, there is a fear that a burden may also be applied to the hand joint which compensates for an overload on the elbow joint, thereby causing tenosynovitis of the hand. However, the stability of the elbow joint is obtained by the wear of the elbow joint supporter 10, whereby it is possible to reduce an overload on other joints such as the hand joint.

In addition, in this embodiment, as the ground knitting yarn which is used in the moss stitch, the tuck stitch, and the mesh stitch, an upper thread which is nylon yarn having a thickness of 70 deniers and is composed of two pieces of knitting yarn, an under thread which is nylon yarn having a thickness of 30 deniers and is composed of two pieces of knitting yarn, and a rubber thread which is covering yarn (DCY: double covered yarn) in which two pieces of nylon winding yarn each having a thickness of 40 deniers are wound around polyurethane core yarn having a thickness of 260 deniers are used. However, the threads are not limited to these materials.

For example, as the upper thread, it is preferable to select a natural fiber such as cotton, wool (cashmere, lamb, Angora, or the like), silk, or hemp, a chemical fiber such as acrylic, a material having a sweat absorbing, quick-drying, or body temperature adjusting function, or the like according to the cost of the elbow joint supporter 10 or the needs of a wearer. Further, as the under thread, it is preferable to select an ester, FTY (filament twisted yarn), or an antibacterial, deodorant, or odor eliminating material according to the cost of the elbow joint supporter 10 or the needs of a wearer.

Further, the woolly nylon yarn (pattern yarn) in the tuck stitch-plating stitch knitted fabric (the supporting section 4) is composed of two pieces of knitting yarn each having a thickness of 100 deniers.

In addition, a knitted fabric of the boundary between the base fabric section 1 and the supporting section 4 related to this embodiment is knitted such that an upper thread which is used in the base fabric section 1 and an upper thread which is used in the supporting section 4 are continuous without overlapping each other, as shown in FIG. 1(a). However, as shown in FIG. 8(a), a knitted fabric 6 of the boundary between the base fabric section 1 and the supporting section 4 is knitted by overlapping an upper thread which is used in the base fabric section 1 and an upper thread which is used in the supporting section 4 and using the upper threads along with a common under thread which is used in the base fabric section 1 and the supporting section 4. Further, a knitted fabric of the boundary between the base fabric section 1 and the olecranon contact section 5 is knitted such that an upper thread which is used in the base fabric section 1 and an upper thread which is used in the olecranon contact section 5 are continuous without overlapping each other, as shown in FIG. 1(b), or as shown in FIG. 8(b), the knitted fabric 6 of the boundary between the base fabric section 1 and the olecranon contact section 5 is knitted by overlapping an upper thread which is used in the base fabric section 1 and an upper thread which is used in the olecranon contact section 5 and using the upper threads along with a common under thread which is used in the base fabric section 1 and the olecranon contact section 5. In particular, in the knitting shown in FIG. 8(b), since the knitted fabric 6 reinforces the boundary between the base fabric section 1 and the olecranon contact section 5, in which expansion and contraction by the flexion and extension of the elbow joint are largest and a load is largest, a fray, a break, or the like of the boundary can be prevented.

Figure 3A:
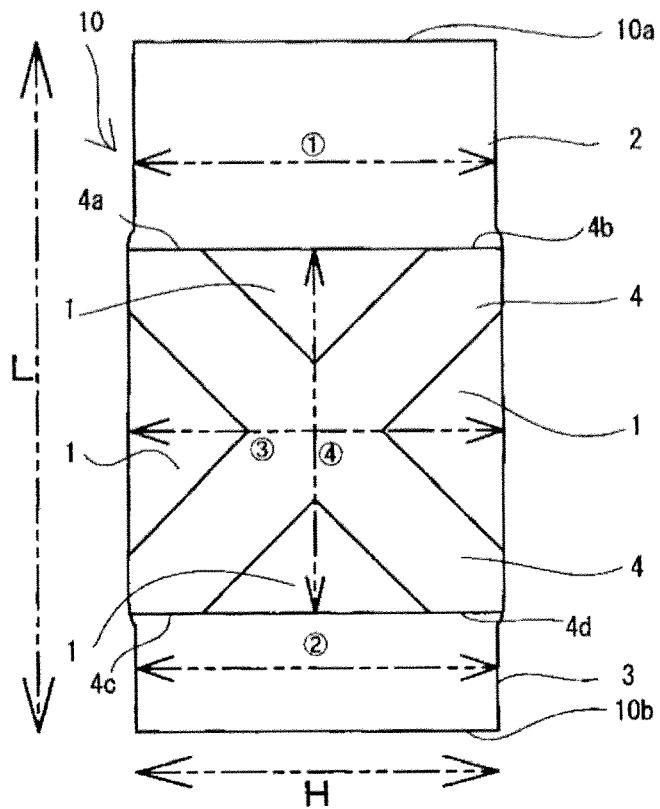
FIG. 3(a) is an explanatory diagram for describing sites for measuring an elongation rate in the elbow joint supporter shown in FIG. 1(a)
Figure 3B:
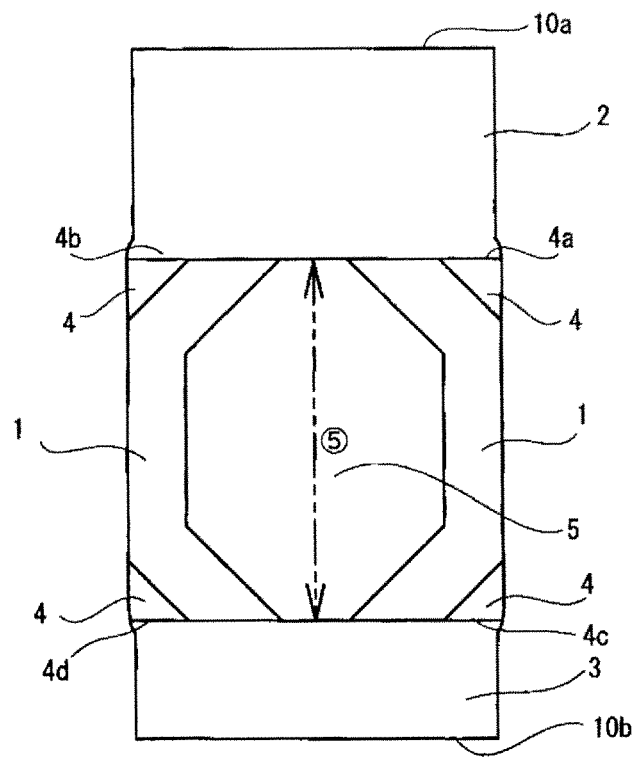
FIG. 3(b) is an explanatory diagram for describing sites for measuring an elongation rate in the elbow joint supporter shown in FIG. 1(b).

Here, the results of measurement of an elongation rate (the percentage of a difference between a length when elongated (an elongated dimension) and the original length (the original dimension) to the original length) measured with respect to the respective site (refer to FIG. 3) of the elbow joint supporter 10 made according to the above-described knitting yarn and knitted fabrics by using a stretch tester (tensile load: 4 kg) are shown in Table 1 below.

TABLE 1

| Measured site | | Original dimension [cm] | Elongated dimension [cm] | Elongation rate [%] |
| --- | --- | --- | --- | --- |
| Circled number 1 | Circumferential direction H of the first anchor section 2 | 11.3 | 34.5 | 205.3 |
| Circled number 2 | Circumferential direction H of the second anchor section 3 | 10.6 | 30.5 | 187.7 |
| Circled number 3 | Circumferential direction H passing through a crossing portion of the supporting section 4 and over the supporting section 4 and the base fabric section 1 | 12.2 | 28.5 | 133.6 |
| Circled number 4 | Length direction L passing through a crossing portion of the supporting section 4 and over the supporting section 4 and the base fabric section 1 | 10.7 | 21.0 | 96.2 |
| Circled number 5 | Length direction L of the olecranon contact section 5 | 10.7 | 38.0 | 255.1 |

In addition, since the elongation rate in Table 1 represents the fact that the larger the value, the more easily the knitted fabric is elongated and the tension F in the above-described expression (1) represents the fact that the larger the value, the more difficult it is for the knitted fabric to be elongated (the larger the tightening force), an inequality sign show the magnitude relation of the elongation rate and an inequality sign showing the magnitude relation of the tension F become opposite to each other.

Next, the result of verification of the operation and effects of the elbow joint supporter 10 related to this embodiment will be described.

Figure 4A:
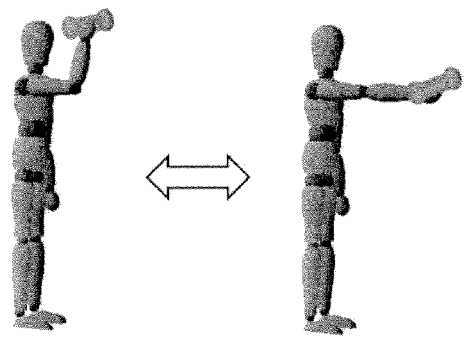
FIG. 4(a) is an explanatory diagram for describing an experimental motion.

In the first experiment, in a case where the elbow joint supporter 10 is worn on the right elbow of a test subject (a 26-years-old healthy male, there is no anamnesis in four limbs) (hereinafter referred to as the time of wear) and a case where the elbow joint supporter 10 is not worn (hereinafter referred to as the time of non-wear), the elbow joint was flexed and extended three times in a state where a dumbbell (an iron dumbbell) of 4 kg is held by the right hand and the brachium of the right arm is approximately horizontal (FIG. 4(a)).

Figure 4B:
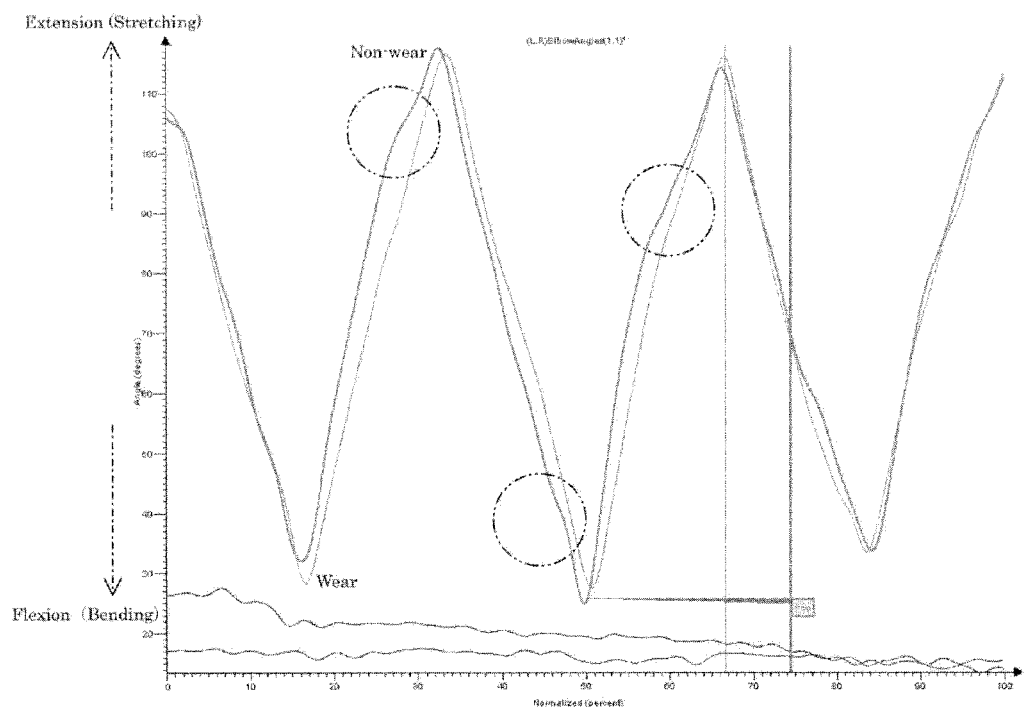
FIG. 4(b) is a graph showing the verification results by three-dimensional motion analysis in the elbow joint supporter shown in FIG. 1.

At this time, in the experiment, the trajectory of an angle by the flexion and extension (bending and stretching) of the elbow joint was measured by three-dimensional motion analysis (FIG. 4(b)) and the myogenic potentials of the biceps brachii muscle (the muscle to bend the elbow) and the flexor carpi ulnaris muscle and the flexor carpi radialis muscle (the muscles to bend the wrist) in the third bending and stretching motion were measured by a surface electromyogram (FIG. 5).

In addition, in the three-dimensional motion analysis, a three-dimensional motion analysis system "VICON MX" manufactured by VICON, Inc. was used, and in the measurement of the surface electromyogram, "MyoResearch" manufactured by Noraxon, Inc. was used.

As shown in FIG. 4(b), in the case of the time of wear (a thin line shown in FIG. 4(b)), the trajectory of the angle in the flexion and the extension is smooth. However, in the case of the time of non-wear (a thick line shown in FIG. 4(b)), as shown in an area surrounded by a two-dot chain line, since a disturbance is present in a waveform and deflection is present in the trajectory, it can be found that it is a hypertonic state. That is, the elbow joint supporter 10 can improve the stability of the elbow joint of a wearer.

Figure 5A:
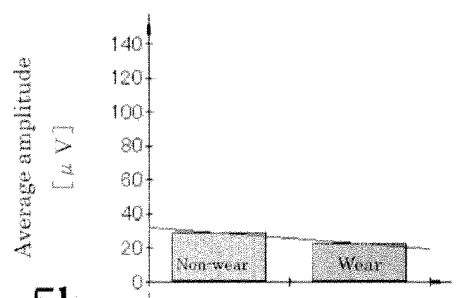
FIG. 5(a) is graphs showing the verification results by a surface electromyogram of the flexor carpi ulnaris muscle in the elbow joint supporter shown in FIG. 1.
Figure 5B:
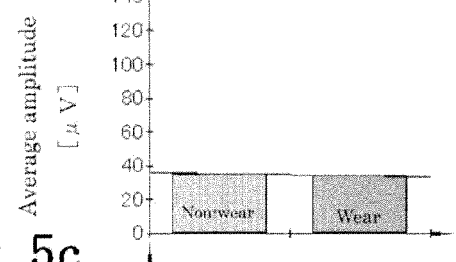
FIG. 5(b) is graphs showing the verification results by a surface electromyogram of the flexor carpi radialis muscle in the elbow joint supporter shown in FIG. 1.
Figure 5C:
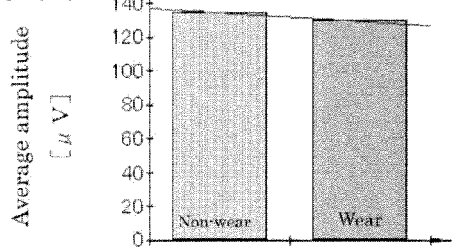
FIG. 5(c) is graphs showing the verification results by a surface electromyogram of the biceps brachii muscle in the elbow joint supporter shown in FIG. 1.
Figure 5C:
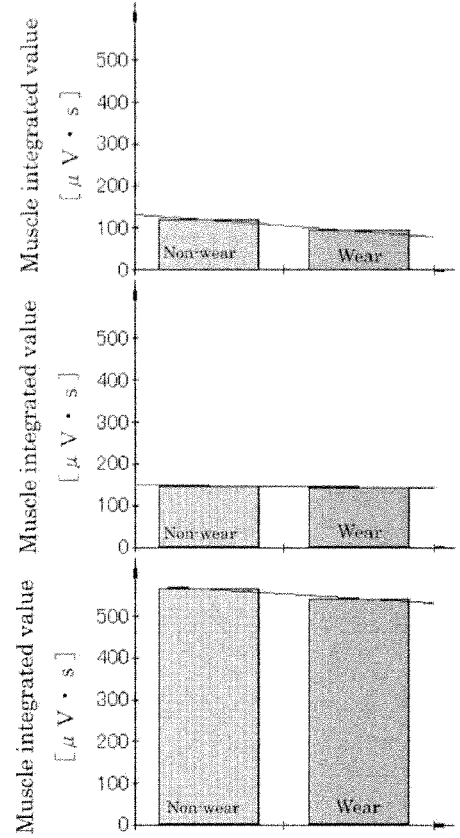

Further, as shown in FIG. 5(c), since in the case of the time of wear, the myogenic potential (the average amplitude and the muscle integrated value) of the biceps brachii muscle is lowered compared to the case of the time of non-wear, it can be found that a load on the biceps brachii muscle is reduced, so that a strain on the elbow joint is reduced. In particular, the elbow joint supporter 10 reduces a strain on the elbow joint, so that it becomes possible to prevent a bicipital tendinitis.

Further, as shown in FIGS. 5(a) and 5(b), since in the case of the time of wear, the myogenic potentials (the average amplitudes and the muscle integrated values) of the flexor carpi ulnaris muscle and the flexor carpi radialis muscle are lowered, compared to the case of the time of non-wear, it can be found that loads on the flexor carpi ulnaris muscle and the flexor carpi radialis muscle are reduced, so that a strain on the hand joint is reduced.

In the second experiment, in a case where the elbow joint supporters 10 are worn on the right elbows of three test subjects (healthy adult males, average age: 29±3.6-years-old, average height: 169.7±4.9 cm, and average weight: 64.3±11.9 kg) (the time of wear) and a case where the elbow joint supporter 10 is not worn (the time of non-wear), the elbow joints of the test subjects were flexed and extended in a state where the brachium of the right arm of each test subject is approximately vertical and the forearm of the right arm of each test subject is approximately horizontal. In the experiment, the amount of work of an elbow joint flexion moment of each test subject was measured (FIG. 6), and the amount of work of an elbow joint extension moment of each test subject was measured (FIG. 7).

Figure 6A:
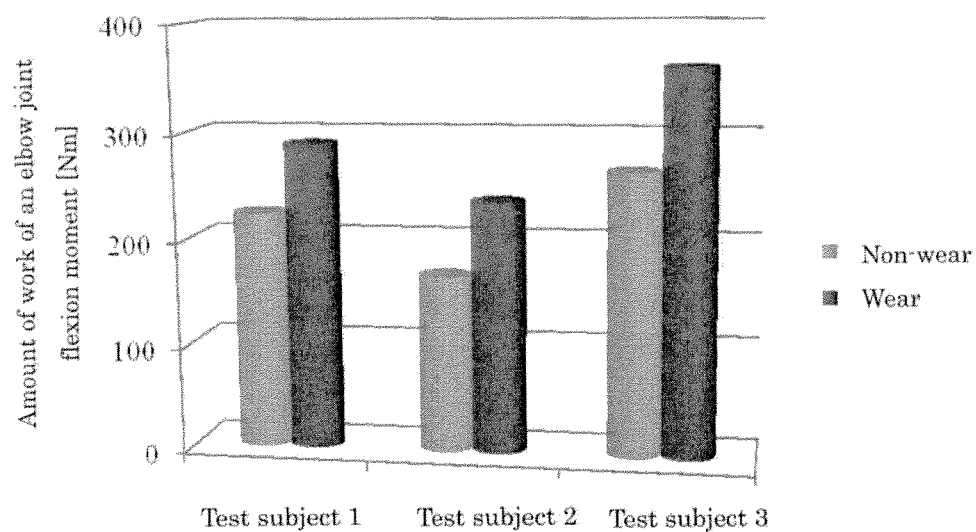
FIG. 6(a) is a graph showing the measurement results of the amount of work of an elbow joint flexion moment with respect to each test subject for verifying the operation and effects of the elbow joint supporter shown in FIG. 1.
Figure 6B:
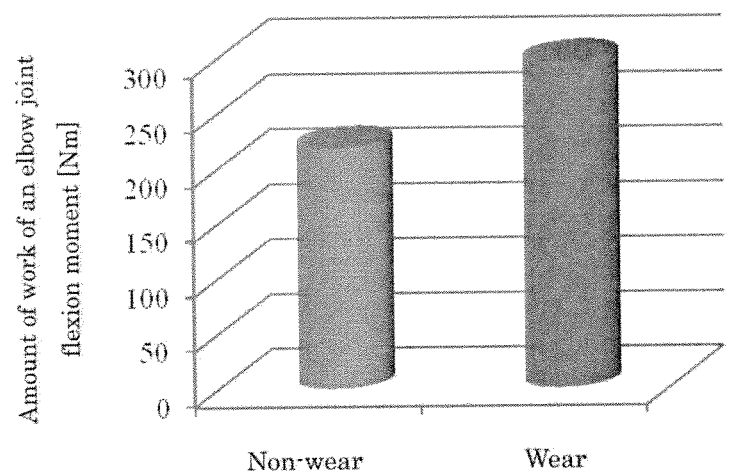
FIG. 6(b) is a graph showing the average value of the measurement results shown in FIG. 6(a).
Figure 7A:
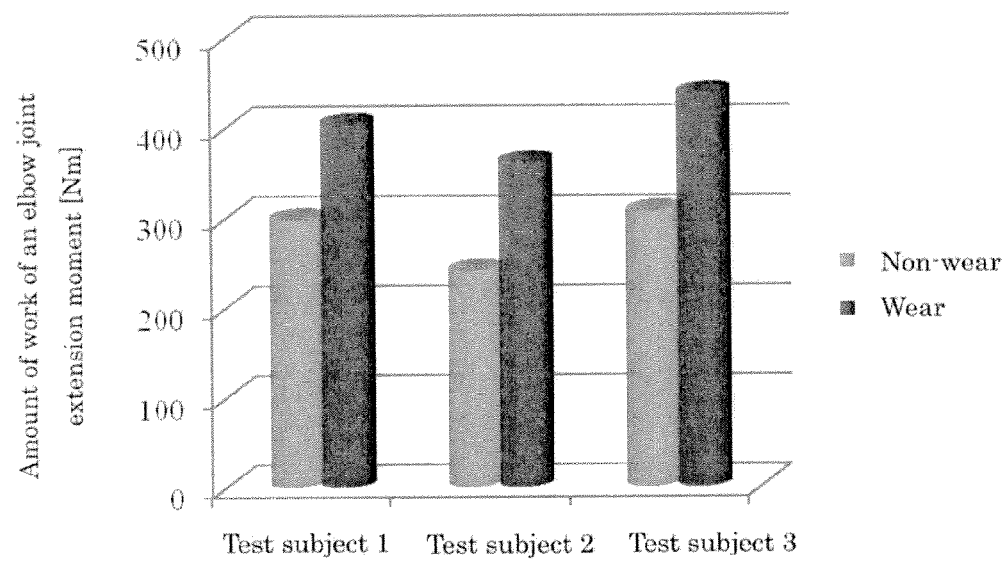
FIG. 7(a) is a graph showing the measurement results of the amount of work of an elbow joint extension moment with respect to each test subject for verifying the operation and effects of the elbow joint supporter shown in FIG. 1.
Figure 7B:
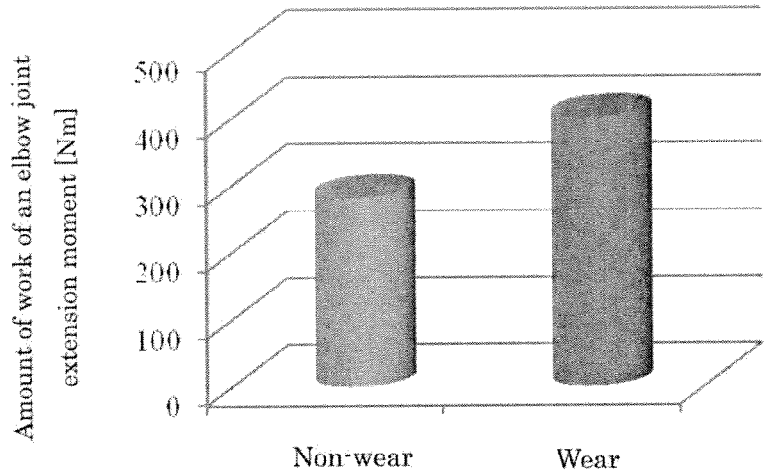
FIG. 7(b) is a graph showing the average value of the measurement results shown in FIG. 7(a).

As shown in FIGS. 6 and 7, it can be found that in all the test subjects, at the time when the elbow joint supporter 10 is worn, the amount of work of an elbow joint flexion moment and the amount of work of an elbow joint extension moment become large compared to the time of non-wear.

(Second Embodiment of the Invention)

FIG. 9(a) is a front view showing the schematic configuration of an elbow joint supporter related to the second embodiment, FIG. 9(b) is a back view of the elbow joint supporter shown in FIG. 9(a), FIG. 9(c) is a left side view and right side view of the elbow joint supporter shown in FIG. 9(a), and FIG. 9(d) is a plan view and bottom view of the elbow supporter shown in FIG. 9(a). In FIG. 9, the same symbol as that in FIG. 1, 2, or 8 denotes the same or equivalent section, and explanation thereof is omitted.

In FIG. 9 described above, the elbow joint supporter 10 related to this embodiment is configured to have, in addition to the configuration in the first embodiment described above, reinforcing sections 7 which are knitted to extend in the length direction of the tubular knitted fabric at both side portions on the front face side of the tubular knitted fabric and connected to the first anchor section 2 and the second anchor section 3, thereby reinforcing the supporting section 4.

In a knitted fabric of the reinforcing section 7, expansion and contraction of the reinforcing section 7 in the length direction L of the elbow joint supporter 10 is moderately suppressed, for example, by additionally feeding another knitting yarn (for example, woolly nylon yarn) in addition to the knitting yarn of the base fabric section 1 (the tuck stitch knitted fabric) and the supporting section 4 (the tuck stitch-plating stitch knitted fabric), which constitute the reinforcing section 7, and another knitting yarn is cut at the boundary between the reinforcing section 7 and the base fabric section 1 and the supporting section 4 (a cut boss).

Further, it is also conceivable that the reinforcing section 7 is constituted by knitting a knitted fabric by yarn impregnated with resin of a kind such as a polyester type, a polyamide type, a polyurethane type, a polyethylene type (high density, low density), or an ethylene vinyl acetate type.

Further, it is also conceivable that the reinforcing section 7 is constituted by sewing a tape made of a narrow cloth or the like for preventing elongation to the knitted fabrics of the base fabric section 1 (the tuck stitch knitted fabric) and the supporting section 4 (the tuck stitch-plating stitch knitted fabric), which constitute the reinforcing section 7, or by sticking an adhesive tape in which an adhesive is applied onto a tape made of cellophane, plastic, or the like, to the knitted fabrics of the base fabric section 1 and the supporting section 4.

Further, it is also conceivable that the reinforcing section 7 is constituted by applying liquid resin to the knitted fabrics of the base fabric section 1 (the tuck stitch knitted fabric) and the supporting section 4 (the tuck stitch-plating stitch knitted fabric), which constitute the reinforcing section 7, and then bringing the resin into contact with air, thereby oxidizing and fixing the resin, or by attaching a thin film-shaped resin to the knitted fabrics of the base fabric section 1 and the supporting section 4, or by spraying liquid resin onto the knitted fabrics of the base fabric section 1 and the supporting section 4 by a sprayer or the like, and then bringing the resin into contact with air, thereby oxidizing and fixing the resin.

Further, the reinforcing section 7 may also be an adhesive interlining cloth which is obtained by performing resin processing on the knitted fabrics of the base fabric section 1 (the tuck stitch knitted fabric) and the supporting section 4 (the tuck stitch-plating stitch knitted fabric), which constitute the reinforcing section 7, by using an adhesive. In this case, the resin can be fixed to the knitted fabrics by applying adhesive resin made of resin of a kind such as a polyester type, a polyamide type, a polyurethane type, a polyethylene type (high density, low density), or an ethylene vinyl acetate type to the knitted fabrics by a processing method such as dot processing, powder processing, cobweb processing, or film processing and then performing heating and pressurization treatments by a flat press, a roller-type press, or the like.

In addition, the second embodiment is different from the first embodiment only in that the reinforcing section 7 is newly disposed on the front face side of the elbow joint supporter 10, and except the operation and effects by the reinforcing section 7, which are described below, the same operation and effects as those in the first embodiment are obtained.

As previously described in the first embodiment, since in the cubital fossa of a wearer, a range of joint motion of flexion and extension of the elbow joint with respect to the entire elbow is the widest, if the area of the supporting section 4 in the cubital fossa is too wide, a state is created where the supporting section 4 with large stretch resistance becomes a large mass and is superimposed on a section of the cubital fossa of the wearer.

For this reason, by disposing the reinforcing sections 7 which connect the first anchor section 2 and the second anchor section 3 to each other, without being superimposed on the cubital fossa of a wearer, it is possible to enhance an action to assist in the flexion and extension of the elbow joint by the supporting section 4.

REFERENCE SIGNS LIST

1: base fabric section
2: first anchor section
3: second anchor section
4: supporting section
4a, 4b, 4c, 4d: end portion
5: olecranon contact section
6: knitted fabric of a boundary
7: reinforcing section
10: elbow joint supporter
10a: upper end
10b: lower end

The invention claimed is:

1. An elbow joint supporter constructed from a tubular knitted fabric that is knitted by circular knitting, and adapted to come into contact with a body surface of a wearer, thereby assisting an elbow joint by improving the stability thereof, the elbow joint supporter comprising:
a first anchor section configured as a knitted fabric which is knitted around a first end of the tubular knitted fabric and adapted to allow the tubular knitted fabric to be tightened on a brachium of the wearer;
a second anchor section configured as a knitted fabric which is knitted around a second end of the tubular knitted fabric and adapted to allow the tubular knitted fabric to be tightened on a forearm of the wearer;
a supporting section includes a front face side which is knitted in an X-shape configuration that is formed of two intersecting portions which covers and is adapted to cross over a cubital fossa of the wearer, and is adapted to support the elbow joint of the wearer by connecting a first two end portions of said supporting section to the first anchor section and connecting a second two end portions of said supporting section to the second anchor section;
a base fabric section which is a knitted fabric surrounded by the first anchor section, the second anchor section, and the supporting section of the tubular knitted fabric; and
an olecranon contact section which is knitted on a rear face side of the tubular knitted fabric and is adapted to contact an olecranon of the wearer;
wherein the base fabric section is a tuck stitch knitted fabric,
the olecranon contact section is a mesh stitch knitted fabric or a bellows knitted fabric,
a stretch resistance of the first anchor section and the second anchor section in a circumferential direction of the tubular knitted fabric is greater than a stretch resistance of the base fabric section in the circumferential direction of the tubular knitted fabric,
a stretch resistance of the supporting section in a length direction of the tubular knitted fabric is greater than a stretch resistance of the base fabric section in the length direction of the tubular knitted fabric,
a first end of the first two end portions of the supporting section connected to the first anchor section at a first position and a second end of the first two end portions of the supporting section connected to the first anchor section at a second position, the first position disposed at a distance from the second position along both a front circumferential direction of the tubular knitted fabric and a rear circumferential direction of the tubular knitted fabric, the first end of the first two end portions and the second end of the first two end portions disposed at a distance from each other along both the front circumferential direction of the tubular knitted fabric and the rear circumferential direction of the tubular knitted fabric;
a first end of the second two end portions of the supporting section connected to the second anchor section at a first position and a second end of the second two end portions of the supporting section connected to the second anchor section at a second position, the first position disposed at a distance from the second position along both the front circumferential direction of the tubular knitted fabric and the rear circumferential direction of the tubular knitted fabric, the first end of the second two end portions and the second end of the second two end portions disposed at a distance from each other along both the front circumferential direction and the rear circumferential direction of the tubular knitted fabric;
the base fabric section is connected to the first anchor section and the second anchor section on the rear face side of the tubular knitted fabric;
the olecranon contact section is surrounded by the base fabric section;
a stretch resistance of the olecranon contact section in the length direction of the tubular knitted fabric is less than the stretch resistance of the base fabric section in the length direction of the tubular knitted fabric; and
the olecranon contact section is configured to absorb forces associated with an expansion and contraction of the skin of the wearer during movement of the elbow joint and prevent a position shift in any direction of the elbow joint supporter.

2. The elbow joint supporter according to claim 1, wherein the supporting section is a knitted fabric in which a tuck stitch knitted fabric and a plating stitch knitted fabric are used in combination.

3. The elbow joint supporter according to claim 1, wherein the olecranon contact section is a knitted fabric in which a mesh stitch knitted fabric and a plain stitch knitted fabric which extend in the circumferential direction of the tubular knitted fabric are alternately arranged in parallel.

4. The elbow joint supporter according to claim 1, wherein a knitted fabric of a boundary of the olecranon contact section is knitted by overlapping an upper thread which is used in the base fabric section and an upper thread which is used in the olecranon contact section and using the upper thread of the base fabric section and the upper thread of the olecranon contact section along with an under thread which is used in both the base fabric section and the olecranon contact section.

5. The elbow joint supporter according to claim 1, further comprising:
reinforcing sections which are knitted to extend in the length direction of the tubular knitted fabric at first and second side portions on the front face side of the tubular knitted fabric and connected to the first anchor section and the second anchor section, thereby reinforcing the supporting section.

6. An elbow joint supporter constructed from a tubular knitted fabric that is knitted by circular knitting, and adapted to come into contact with a body surface of a wearer, thereby assisting an elbow joint by improving the stability thereof, the elbow joint supporter comprising:
a first anchor section configured as a knitted fabric which is knitted around a first end of the tubular knitted fabric and adapted to allow the tubular knitted fabric to be tightened on a brachium of the wearer;

a second anchor section configured as a knitted fabric which is knitted around a second end of the tubular knitted fabric and adapted to allow the tubular knitted fabric to be tightened on a forearm of the wearer;

a supporting section includes a front face side which is knitted in an X-shape configuration that is formed of two intersecting portions which covers and is adapted to cross over a cubital fossa of the wearer, and is adapted to support the elbow joint of the wearer by connecting a first two end portions of said supporting section to the first anchor section and connecting a second two end portions of said supporting section to the second anchor section;

a base fabric section which is a knitted fabric surrounded by the first anchor section, the second anchor section, and the supporting section of the tubular knitted fabric; and an olecranon contact section which is knitted on a rear face side of the tubular knitted fabric and is adapted to contact an olecranon of the wearer;

wherein the base fabric section is a tuck stitch knitted fabric, the olecranon contact section is a mesh stitch knitted fabric or a bellows knitted fabric, a stretch resistance of the first anchor section and the second anchor section in a circumferential direction of the tubular knitted fabric is greater than a stretch resistance of the base fabric section in the circumferential direction of the tubular knitted fabric;

a stretch resistance of the supporting section in a length direction of the tubular knitted fabric is greater than a stretch resistance of the base fabric section in the length direction of the tubular knitted fabric;

a first end of the first two end portions of the supporting section connected to the first anchor section at a first position and a second end of the first two end portions of the supporting section connected to the first anchor section at a second position, the first position disposed at a distance from the second position along both a front circumferential direction of the tubular knitted fabric and a rear circumferential direction of the tubular knitted fabric, the first end of the first two end portions and the second end of the first two end portions disposed at a distance from each other along both the front circumferential direction of the tubular knitted fabric and the rear circumferential direction of the tubular knitted fabric;

a first end of the second two end portions of the supporting section connected to the second anchor section at a first position and a second end of the second two end portions of the supporting section connected to the second anchor section at a second position, the first position disposed at a distance from the second position along both the front circumferential direction of the tubular knitted fabric and the rear circumferential direction of the tubular knitted fabric, the first end of the second two end portions and the second end of the second two end portions disposed at a distance from each other along both the front circumferential direction and the rear circumferential direction of the tubular knitted fabric;

the base fabric section is connected to the first anchor section and the second anchor section on the rear face side of the tubular knitted fabric;

the olecranon contact section is connected to the first anchor section and the second anchor section together with the base fabric section;

a stretch resistance of the olecranon contact section in the length direction of the tubular knitted fabric is less than the stretch resistance of the base fabric section in the length direction of the tubular knitted fabric; and the olecranon contact section is configured to absorb forces associated with an expansion and contraction of the skin of the wearer during movement of the elbow joint and prevent a position shift in any direction of the elbow joint supporter.

7. The elbow joint supporter according to claim 6, wherein a knitted fabric of a boundary of the olecranon contact section is knitted by overlapping an upper thread which is used in the base fabric section and an upper thread which is used in the olecranon contact section and using the upper thread of the base fabric section and the upper thread of the olecranon contact section along with an under thread which is used in both the base fabric section and the olecranon contact section.

8. The elbow joint supporter according to claim 6, further comprising:

reinforcing sections which are knitted to extend in the length direction of the tubular knitted fabric at first and second side portions on the front face side of the tubular knitted fabric and connected to the first anchor section and the second anchor section, thereby reinforcing the supporting section.

9. The elbow joint supporter according to claim 1, wherein the olecranon contact section is knitted in one of an oval, elliptical, circular, or elongated configuration on the rear face side of the tubular knitted fabric and is adapted to cover the olecranon of the wearer.

10. The elbow joint supporter according to claim 6, wherein the supporting section is a knitted fabric in which a tuck stitch knitted fabric and a plating stitch knitted fabric are used in combination.

11. The elbow joint supporter according to claim 6, wherein the olecranon contact section is knitted in one of an oval, elliptical, circular, or elongated configuration on the rear face side of the tubular knitted fabric and is adapted to cover the olecranon of the wearer.

12. The elbow joint supporter according to claim 6, wherein the olecranon contact section is a knitted fabric in which a mesh stitch knitted fabric and a plain stitch knitted fabric which extend in the circumferential direction of the tubular knitted fabric are alternately arranged in parallel.

13. The elbow joint supporter according to claim 1, wherein a tension in the length direction of the tubular knitted fabric of an area on the front face side of the tubular knitted fabric, which is occupied by the base fabric section and the supporting section, is larger than a tension in the length direction of the tubular knitted fabric of an area on the rear face side of the tubular knitted fabric, which is occupied by the olecranon contact section and the base fabric section.

14. The elbow joint supporter according to claim 6, wherein a tension in the length direction of the tubular knitted fabric of an area on the front face side of the tubular knitted fabric which is occupied by the base fabric section and the supporting section is larger than a tension in the length direction of the tubular knitted fabric of an area on the rear face side of the tubular knitted fabric which is occupied by the olecranon contact section and the base fabric section.

15. The elbow joint supporter according to claim 13, wherein the stretch resistance of the supporting section along the length direction of the tubular knitted fabric is configured to support a cubital fossa of the wearer by securing the elbow joint of the wearer.

16. The elbow joint supporter according to claim 14, wherein the stretch resistance of the supporting section along the length direction of the tubular knitted fabric is configured to support a cubital fossa of the wearer by securing the elbow joint of the wearer.

* * * * *